US009669175B2

(12) United States Patent
Olympio

(10) Patent No.: US 9,669,175 B2
(45) Date of Patent: Jun. 6, 2017

(54) DEVICES WITH MOUTHPIECES THAT ALLOW FOR RAPID CHANGE OUT OF ENDOTRACHEAL (ET) TUBES AND RELATED METHODS

(71) Applicant: Wake Forest University Health Sciences, Winston-Salem, NC (US)

(72) Inventor: Michael A. Olympio, Winston-Salem, NC (US)

(73) Assignee: Michael A. Olympio, Winston-Salem, NC (US)

( * ) Notice: Subject to any disclaimer, the term of this patent is extended or adjusted under 35 U.S.C. 154(b) by 656 days.

(21) Appl. No.: 14/104,481

(22) Filed: Dec. 12, 2013

(65) Prior Publication Data

US 2014/0166000 A1    Jun. 19, 2014

Related U.S. Application Data

(60) Provisional application No. 61/738,583, filed on Dec. 18, 2012, provisional application No. 61/766,790, filed on Feb. 20, 2013.

(51) Int. Cl.
*A61M 16/04* (2006.01)
*A61M 25/02* (2006.01)
*A61M 25/01* (2006.01)

(52) U.S. Cl.
CPC .... *A61M 16/0493* (2014.02); *A61M 16/0488* (2013.01); *A61M 2025/0183* (2013.01)

(58) Field of Classification Search
CPC ........ A61M 16/0488; A61M 16/049–16/0497; A61M 25/0097; A61M 25/0169; A61M 2025/022; A61M 2025/0183
See application file for complete search history.

(56) References Cited

U.S. PATENT DOCUMENTS

| | | | | |
|---|---|---|---|---|
| 4,270,529 | A | * | 6/1981 | Muto ................ A61M 16/0488 128/200.26 |
| 4,473,067 | A | * | 9/1984 | Schiff ............... A61M 39/0606 600/18 |
| 4,687,470 | A | * | 8/1987 | Okada .................. A61M 25/02 128/DIG. 26 |
| 4,848,331 | A | * | 7/1989 | Northway-Meyer ......................... A61M 16/0488 128/200.26 |

(Continued)

FOREIGN PATENT DOCUMENTS

WO        WO 97/18002 A1    5/1997

OTHER PUBLICATIONS

Extended European Search Report corresponding to European Patent Application No. 13864925.6 (8 pages) (dated Jul. 4, 2016).

(Continued)

*Primary Examiner* — Valerie L Woodward
(74) *Attorney, Agent, or Firm* — Myers Bigel, P.A.

(57) ABSTRACT

Tracheal assembly devices include: (a) a mouthpiece sized and configured to allow an endotracheal tube to extend outwardly therefrom; and (b) a cutting blade in communication with an outwardly facing portion of the mouthpiece. The mouthpiece can include at least one outwardly projecting substantially rigid short tube defining an open channel. The short tube can be configured to allow the endotracheal tube to slidably move therethrough. The cutting blade may be held in a handle releasably attached to the short tube.

23 Claims, 10 Drawing Sheets

(56) References Cited

U.S. PATENT DOCUMENTS

| | | | |
|---|---|---|---|
| 4,960,122 A | 10/1990 | Mizus | |
| 4,997,424 A * | 3/1991 | Little | A61M 25/0668 30/90.4 |
| 5,052,386 A | 10/1991 | Fischer | |
| 5,188,606 A | 2/1993 | Maloney et al. | |
| 5,211,655 A | 5/1993 | Hasson | |
| 5,330,460 A | 7/1994 | Moss et al. | |
| 5,636,625 A | 6/1997 | Miyagi et al. | |
| 5,829,430 A * | 11/1998 | Islava | A61M 16/0488 128/200.26 |
| 5,873,858 A * | 2/1999 | Schafer | A61M 16/0488 128/207.14 |
| 6,159,198 A * | 12/2000 | Gardeski | A61M 25/0668 604/161 |
| 6,497,681 B1 | 12/2002 | Brenner | |
| 7,950,155 B2 * | 5/2011 | Goode | A61F 2/4611 30/280 |
| 2006/0272647 A1 * | 12/2006 | Hauge | A61M 16/0488 128/207.16 |
| 2008/0092901 A1 | 4/2008 | Kang | |
| 2009/0049698 A1 | 2/2009 | Drake et al. | |
| 2009/0084377 A1 * | 4/2009 | Hajgato | A61M 16/0493 128/200.26 |
| 2009/0253964 A1 | 10/2009 | Miyamoto | |
| 2009/0255538 A1 * | 10/2009 | Thomson | A61M 16/0488 128/207.17 |
| 2010/0213241 A1 | 8/2010 | Bedi | |
| 2015/0283344 A1 | 10/2015 | Olympio | |

OTHER PUBLICATIONS

International Search Report and Written Opinion for corresponding PCT Application No. PCT/US2013/075386, date of mailing Apr. 3, 2014.

Endotracheal Tube Holder, Product Example, GMEDI Co. Ltd., http://www.gobizkorea.com/catalog/product_list, date unknown but believed to be before the priority date of the present application, printed from the internet Nov. 19, 2012, 2 pages.

Hudes et al., Difficult Endotracheal Reintubations: A Simple Technique, Anesthesiology, 1986, pp. 515-517, vol. 64.

Wade et al., A Simulation Trial of Fiberoptic Assisted Coaxial Endotracheal Tube Exchange (FACETTE), Abstract and Slides, presented to the Joint Society for Technology in Anesthesia with International Meeting on Medical Simulation (IMMS), 2004, 14 pages.

Wade et al., Fiberoptic Assisted Coaxial Endotracheal Tube Exchange (FACETTE), presentation, presented to the Joint Society for Technology in Anesthesia with International Meeting on Medical Simulation (IMMS), 2004, 27 pages.

* cited by examiner

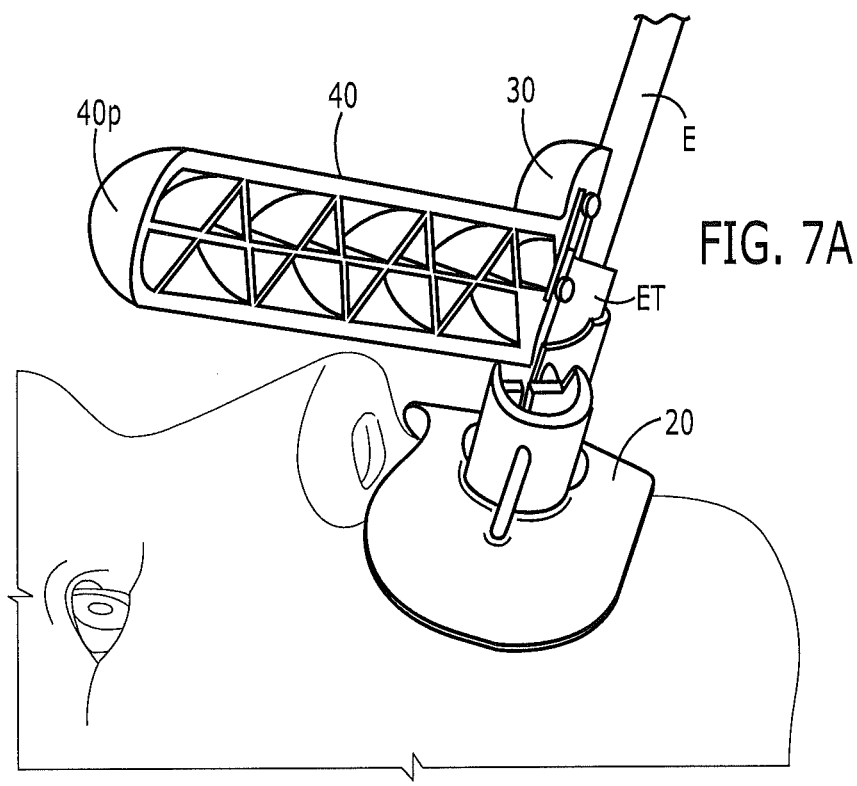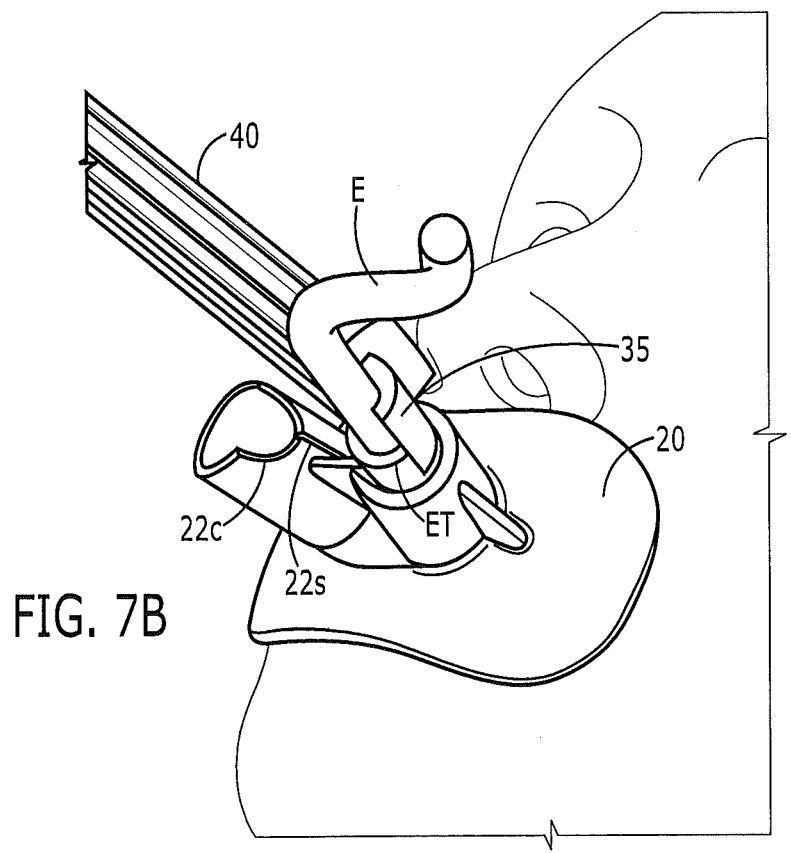

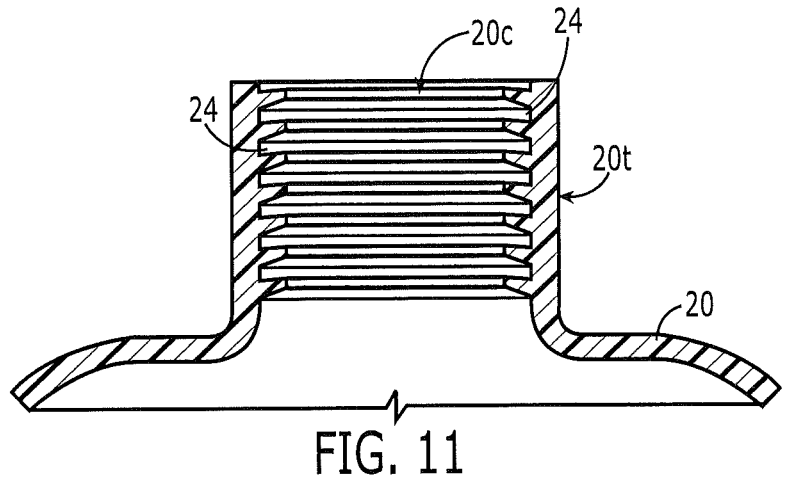
FIG. 11
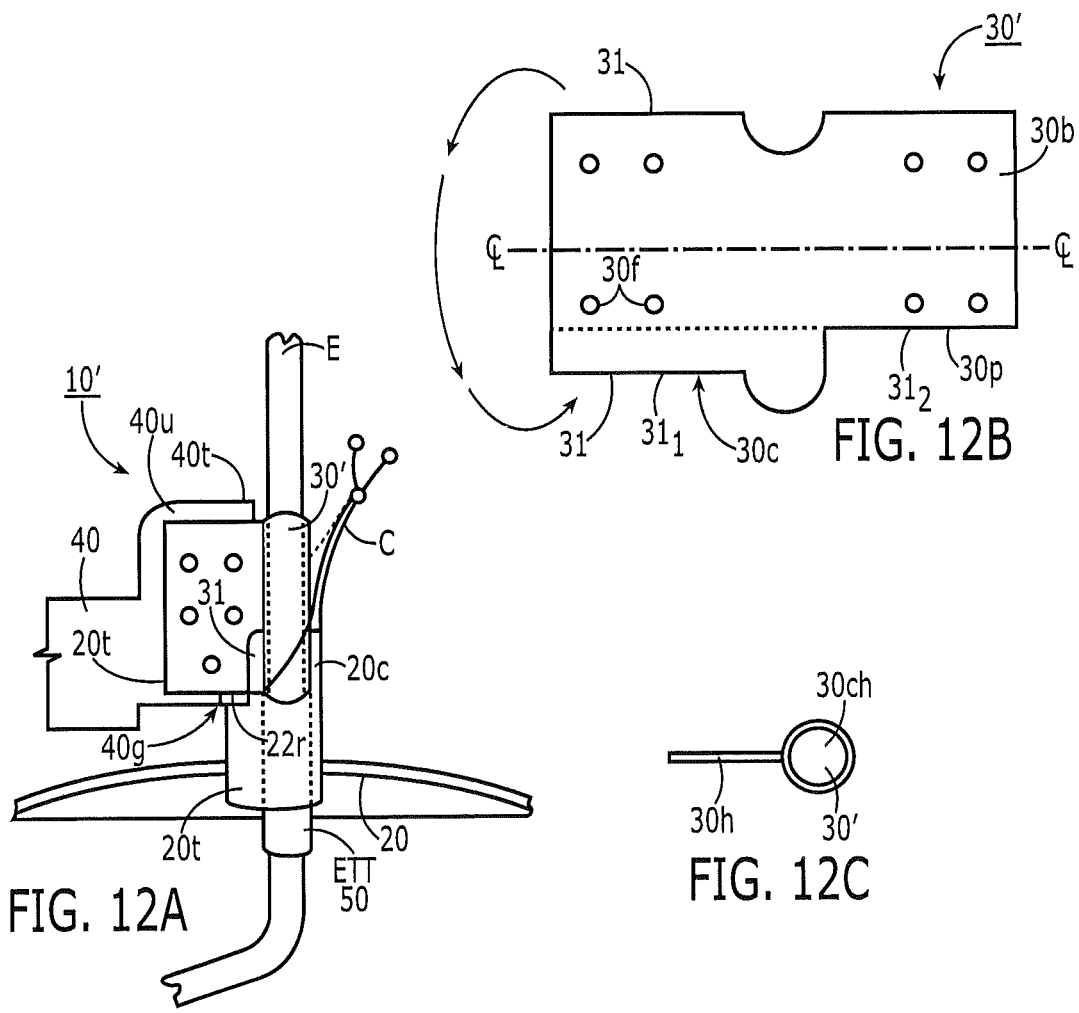
FIG. 12B
FIG. 12A
FIG. 12C

DEVICES WITH MOUTHPIECES THAT ALLOW FOR RAPID CHANGE OUT OF ENDOTRACHEAL (ET) TUBES AND RELATED METHODS

RELATED APPLICATIONS

This application claims the benefit of and priority to U.S. Provisional Application Ser. No. 61/738,583, filed Dec. 18, 2012 and U.S. Provisional Application Ser. No. 61/766,790, filed Feb. 20, 2013, the contents of which are hereby incorporated by reference as if recited in full herein.

FIELD OF THE INVENTION

The present invention relates to medical devices.

BACKGROUND

Endotracheal (ET) tubes are used to protect a patient's airway. An ET tube can be connected to a ventilator to help the patient breathe. Often, once the ET tube is in position, it remains in position and holds the patient's airway open. If the ET tube is prematurely removed, the airway can swell shut. Unfortunately, over time, the ET tube can be a pathway for bacteria or other undesired pathogens or may become somewhat occluded by biofilms or mucus.

SUMMARY OF EMBODIMENTS OF THE INVENTION

Embodiments of the present invention allow an endotracheal tube to be replaced (changed out) while maintaining the patency of an airway.

Embodiments of the invention are directed to tracheal assembly devices. The devices include: (a) a mouthpiece sized and configured to allow an endotracheal tube to extend outwardly therefrom; and (b) a cutting blade in communication with an outwardly facing portion of the mouthpiece.

The mouthpiece can include at least one outwardly projecting substantially rigid short tube defining an open channel. The short tube can be configured to allow the endotracheal tube to slidably move therethrough.

The device can include a handle with first and second matably connecting members that attach together and hold the cutting blade and the handle can releasably engage the mouthpiece.

The mouthpiece can include spaced apart first and second short tubes, each defining an open channel. The device can further include a handle with an end portion that is sized to releasably engage a selected one of the at least one short tube so that, when attached to a respective short tube, the handle extends substantially orthogonally to a centerline of the attached short tube.

The mouthpiece can have a monolithic unitary body with an inwardly extending bite block and a pair of outwardly extending short tubes.

The short tubes can have axially extending centerlines that are spaced apart at an angle between 45 and 120 degrees at an outer end thereof.

The mouthpiece can include at least one outwardly extending substantially rigid short tube. The device can include a handle that holds the cutting blade and releasably engages the mouthpiece. The handle can also include a grip member that snugly holds an outerwall of an endoscope extending through the short tube inside the endotracheal tube. The short tube can have a slit that merges into a curved outer edge portion. The handle can have one end that is configured to reside against the short tube with an end portion residing in the curved outer edge portion of the short tube.

A cutting edge of the cutting blade can face the short tube with the endotracheal tube and endoscope residing in the short tube. The cutting blade can extend a distance of between about 0.1 inches to about 2 inches above an upper end of the short tube.

The mouthpiece can include at least one outwardly projecting substantially rigid short tube defining an open channel. The short tube can be configured to allow the endotracheal tube to extend outwardly therefrom (and be slidably removed or inserted via the channel of the tube). An outer end portion of the short tube can have (i) a first side with a curved end that merges into a downwardly extending slit and (ii) a second side with a substantially "V" shaped notch, with the open end of the V facing up.

The cutting blade can be configured as a malleable unitary surgical metallic band that wraps together to define a cylindrical channel that snugly encases an outerwall of an endoscope.

Other embodiments are directed to medical devices. The devices include: (i) a mouthpiece with at least one outwardly projecting substantially rigid short tube defining an open channel, wherein a respective short tube is configured to allow an endotracheal tube to extend outwardly therefrom; and (ii) a handle comprising a cutting blade configured to reside against the mouthpiece short tube so that the cutting blade resides adjacent the endotracheal tube extending therefrom with the cutting blade extending a distance above the mouthpiece short tube.

The handle can include a grip member configured to engage an endoscope residing inside the endotracheal tube at a location above the respective short tube.

The cutting blade can be a surgical metal band that has a cylindrical channel that snugly abuts an endoscope residing inside the endotracheal tube at a location above the respective short tube.

The mouthpiece can include spaced apart first and second short tubes, each defining an open channel. When in operative position, the handle can extend substantially orthogonal to a centerline of the attached short tube.

The mouthpiece can have a monolithic unitary body with an inwardly extending bite block and the at least one substantially rigid short tube can be a pair of spaced apart outwardly extending short tubes. The short tubes can have axially extending centerlines that are spaced apart at an angle between 45 and 120 degrees at an outer end thereof.

The handle can include first and second matably attachable components that position the grip member proximate to but above the short tube.

The at least one short tube can have a slit that merges into a curved outer edge portion. The handle can be configured to reside against the short tube with a portion residing in the curved outer edge portion of the short tube.

A cutting edge of the cutting blade can face the short tube with the endotracheal tube and endoscope residing therein. The cutting blade can extend a distance of between about 0.1 inches to about 2 inches above an end of the short tube.

An outer end portion of the short tube can have (i) a first inner facing side with a curved end that merges into a downwardly extending slit and (ii) a second outer facing side with a substantially "V" shaped notch, with the open end of the V facing up.

Still other embodiments are directed to methods of changing respective endotracheal tubes. The methods include: (a)

cutting an exposed portion of an endotracheal (ET) tube extending out of patient at an angle; then (b) pulling the endotracheal (ET) tube out of patient through a mouthpiece while the mouthpiece is in position on a patient with an endoscope extending therethrough, wherein the mouthpiece includes or is in communication with a cutting blade; (c) cutting a slit in the wall of the ET tube based on the pulling step; (d) removing the ET tube from the patient; then (e) inserting a different ET tube in the patient over the endoscope after the cutting while the mouthpiece remains on the patient, allowing change out of the ET tube while (i) maintaining visualization through the endoscope of a carina at a distal end of the trachea that splits to right and left lung bronchi and concurrently (ii) maintaining direct access within the trachea during the exchange process to thereby provide a clinician reassurance that access and pathway will not be compromised during the exchange.

The method can include, before the cutting, attaching a handle to the mouthpiece. The handle can have a cutting blade and the attaching can be carried out to position a cutting edge of the cutting blade adjacent an outerwall of the ET tube.

The cutting can be carried out to occur proximate to but above the short tube of the mouthpiece.

The pulling can be carried out by attaching forceps to the ET tube at a top portion of a short tube or above the short tube of the mouthpiece and pulling the ET tube at an angle with respect to the short tube to split the ET tube as it contacts the cutting blade. The removing and inserting steps can be carried out in under 1 minute.

The cutting blade can be defined by a malleable surgical metal band that wraps together to define a cylindrical channel. The method can include placing the metal band about an outerwall of an endoscope so that the endoscope resides snugly in the cylindrical channel.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Other systems and/or methods according to embodiments of the invention will be or become apparent to one with skill in the art upon review of the following drawings and detailed description. It is intended that all such additional systems, methods, and/or devices be included within this description, be within the scope of the present invention, and be protected by the accompanying claims.

BRIEF DESCRIPTION OF THE DRAWINGS

Other features of the present invention will be more readily understood from the following detailed description of exemplary embodiments thereof when read in conjunction with the accompanying drawings.

FIG. 7A is a patient right side perspective view of a tracheal assembly similar to that shown in FIG. 4 illustrating the mouthpiece having a different short tube configuration according to embodiments of the present invention.

FIG. 7B is a patient left side perspective view of the tracheal assembly shown in FIG. 7A.

FIG. 11 is a lateral section schematic illustration of an external short tube of the mouthpiece according to embodiments of the present invention.

FIG. 12A is a schematic illustration of another embodiment of a tracheal assembly according to embodiments of the present invention.

FIG. 12B is a side view of an exemplary cutting band that is used to form the cooperating cutting member of the tracheal assembly shown in FIG. 12A.

FIG. 12C is a top view of the cutting band shown in FIG. 12B in a formed configuration.

DETAILED DESCRIPTION OF EMBODIMENTS OF THE INVENTION

Figure 1:
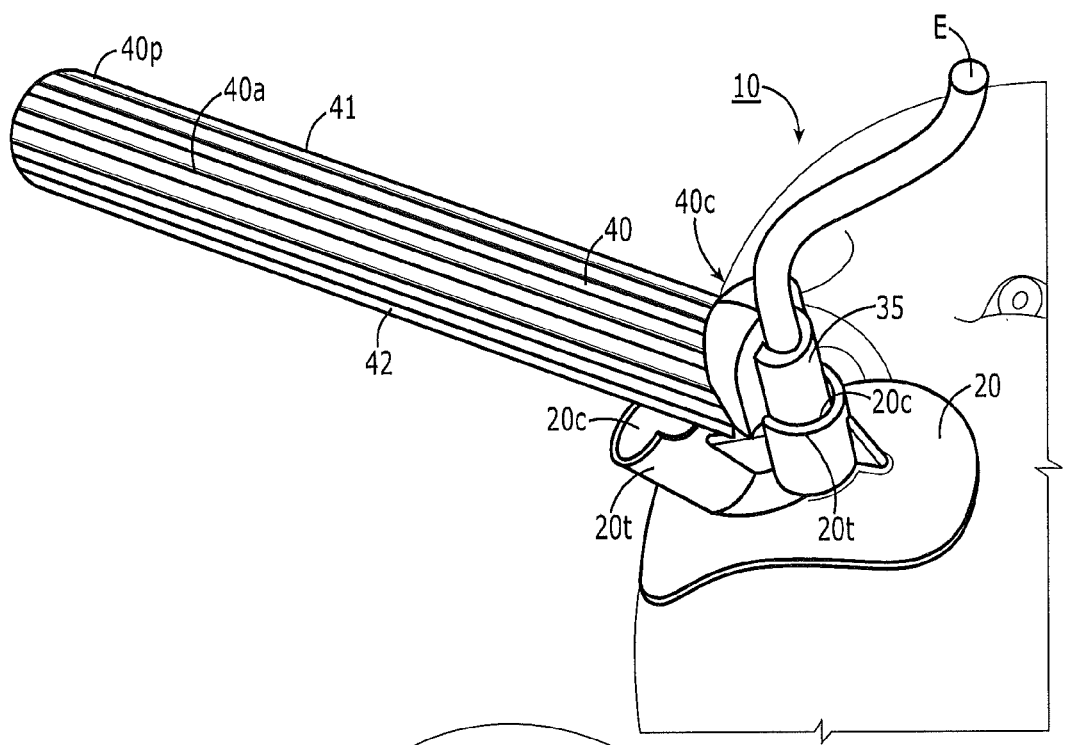
FIG. 1 is a bottom side perspective view of a tracheal assembly according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. One or more features shown and discussed with respect to one embodiment may be included in another embodiment even if not explicitly described or shown with another embodiment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise. In the claims, the word "a" with respect to an element is intended to include one or more of such elements and is not limited to a single such element unless stated otherwise.

The term "about" means that the recited number or value can vary by +/−20%.

The term "sterile" means that the noted device or material meets or exceeds defined medical guidelines of cleanliness and is substantially (if not totally) without contaminants so as to be suitable for medical uses.

The term "short tube" refers to a tube attached or integral to a mouthpiece that has a length that is between about 0.25 inches to about 4 inches, more typically between about 1 to about 2.5 inches.

Figure 2:
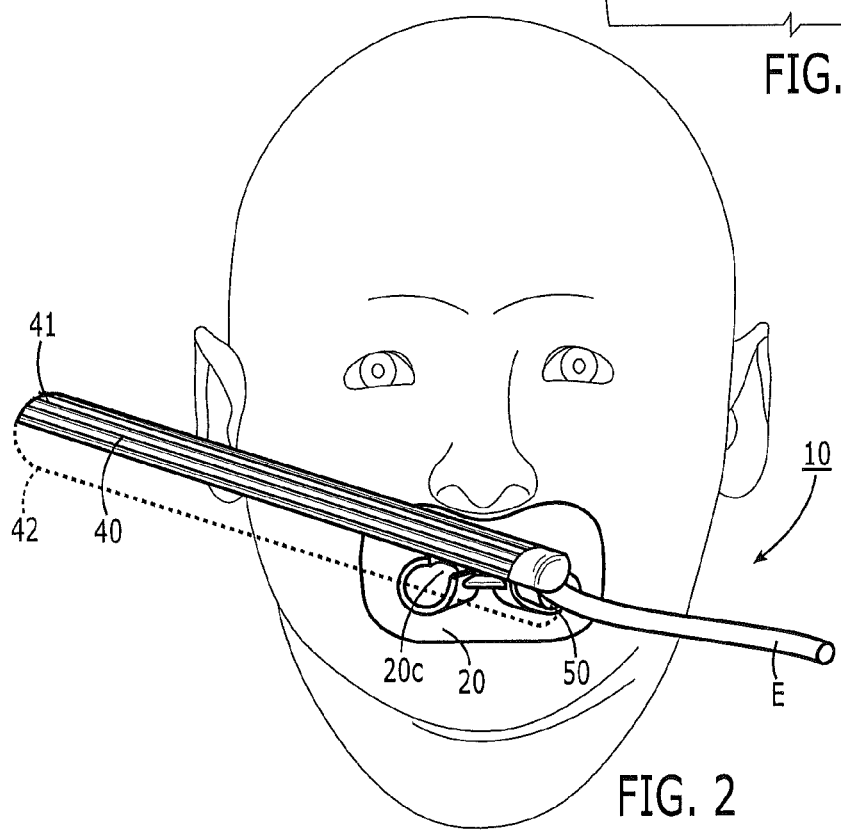
FIG. 2 is a front perspective view of the device shown in FIG. 1, without one (the lower) side of the handle according to embodiments of the present invention.
Figure 3:
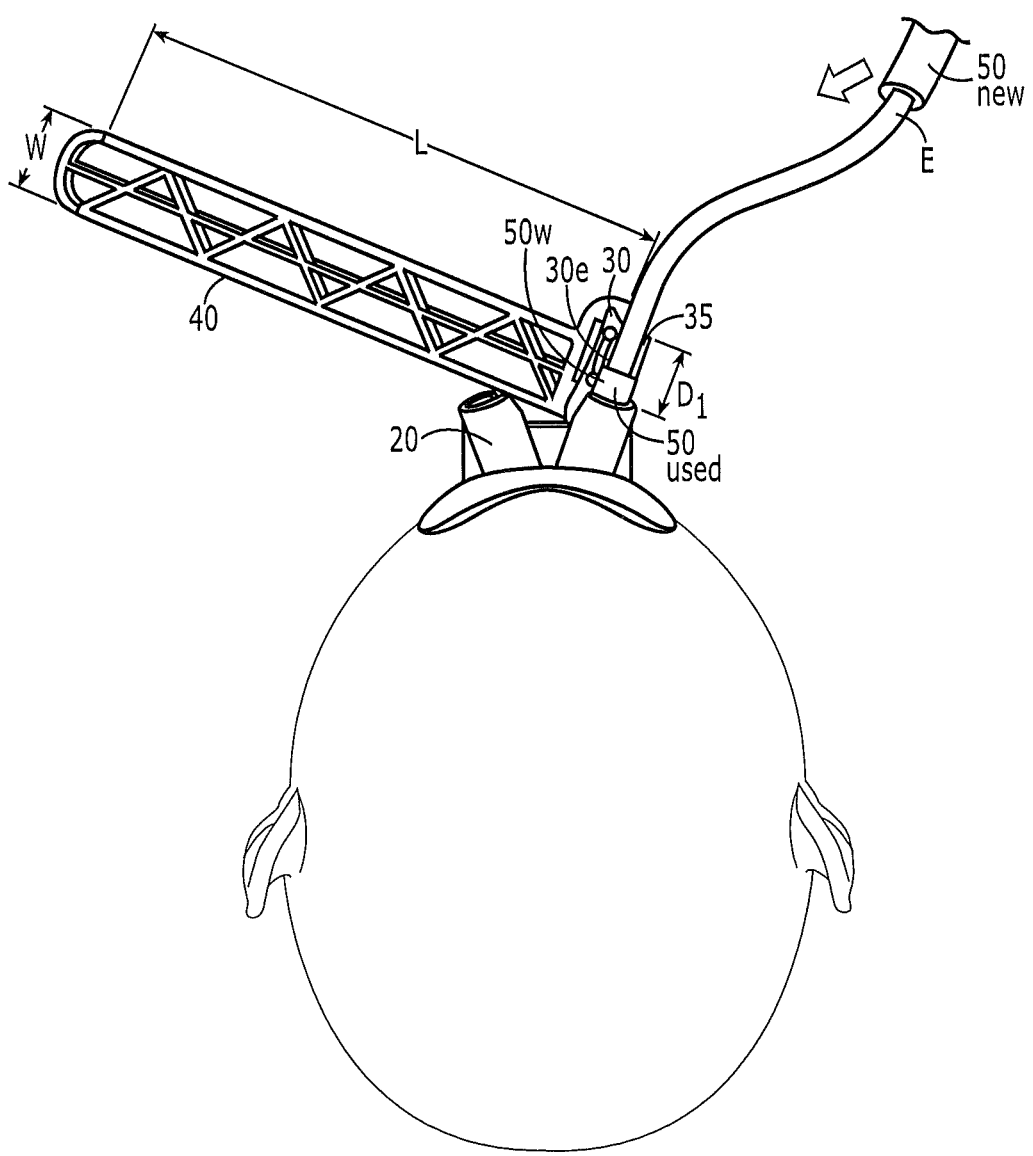
FIG. 3 is a bottom perspective view of the device shown in FIG. 2 according to embodiments of the present invention.

Embodiments of the invention are particularly suitable for human or animal use. Turning now to the figures, FIGS. 1-3 illustrate one embodiment of a tracheal assembly 10. As shown, the tracheal assembly 10 includes a mouthpiece 20. The mouthpiece 20 defines at least one access channel 20c that can slidably receive an endotracheal (ET) tube 50. The device 10 includes a cutting blade 30 that is sized and configured to cut into an outer wall 50w of the ET tube 50 proximate the mouthpiece 20 as the tube 50 is slidably removed from a patient. The cutting blade 30 can have any suitable configuration but is typically a flat razor or scalpel.

Typically, the mouthpiece channel 20c concurrently receives both the ET tube 50 and an endoscope E that extends into the trachea of the patient. The cutting blade 30 faces its cutting edge 30e (FIG. 3) into the channel 20c to be able to cut into a wall 50w of the adjacent ET tube 50 as the ET tube is pulled from the patient over the endoscope E.

Figure 4A:
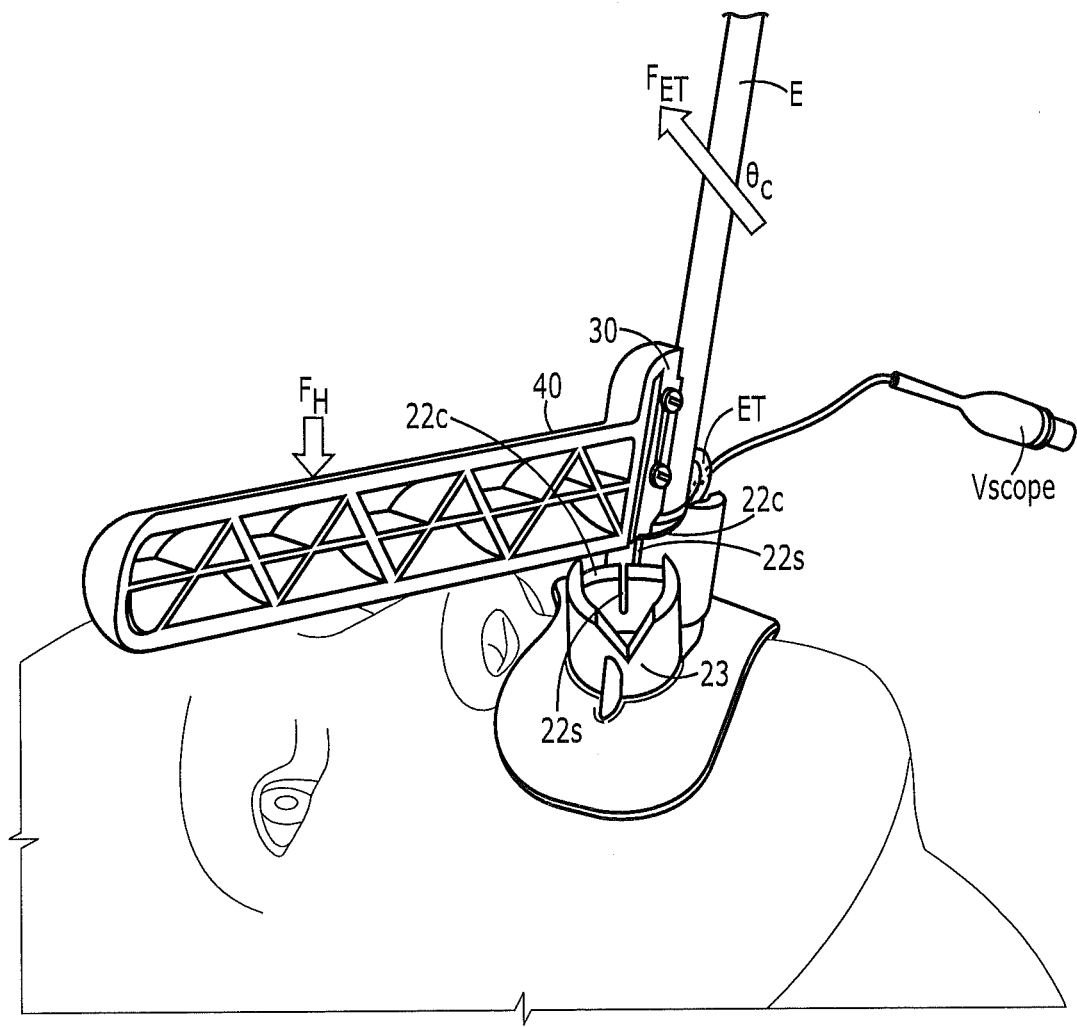
FIG. 4A is a side perspective view of another embodiment of the tracheal assembly device according to embodiments of the present invention.
Figure 4B:
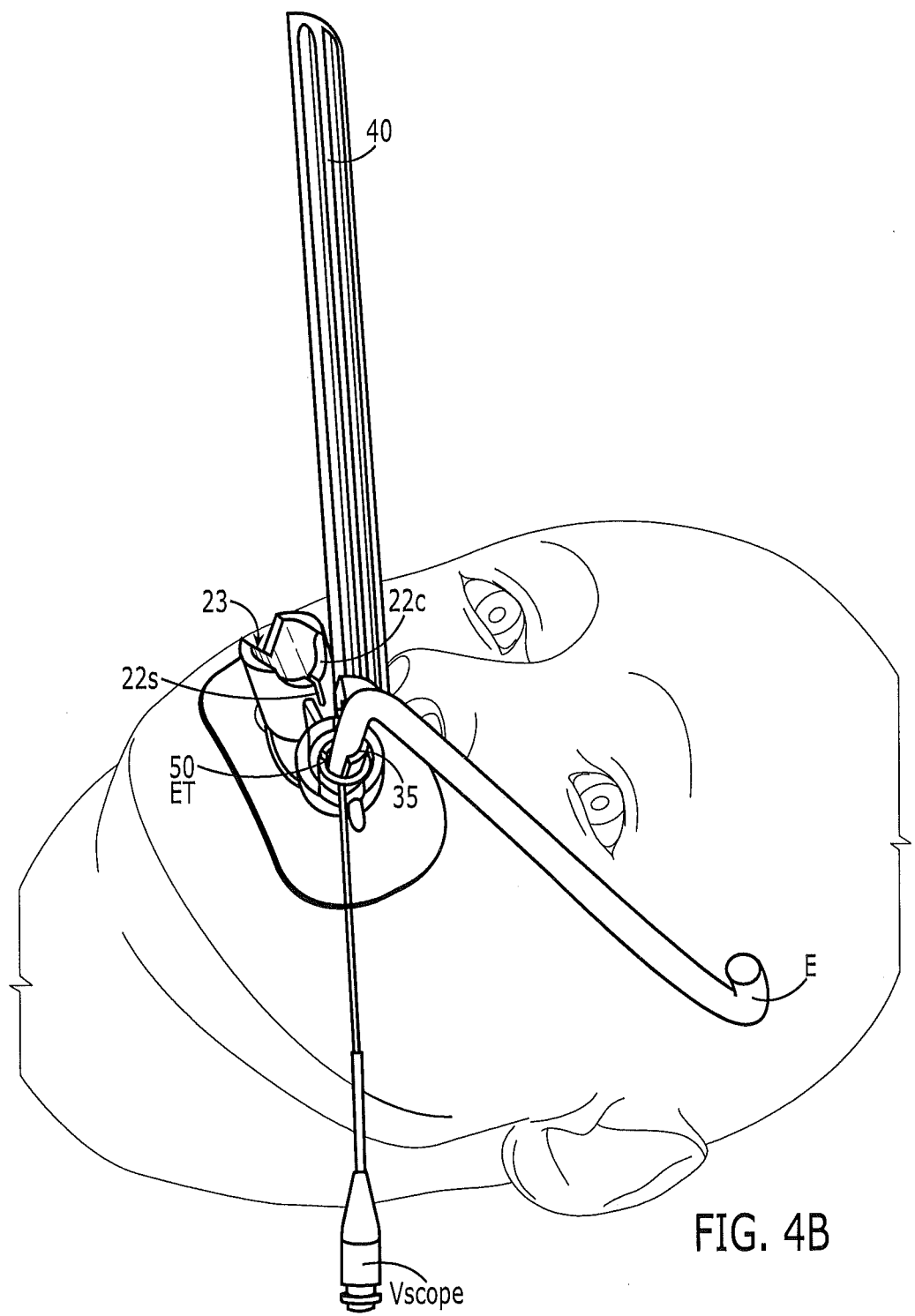
FIG. 4B is an opposing side perspective view from that shown in FIG. 4A.
Figure 6:
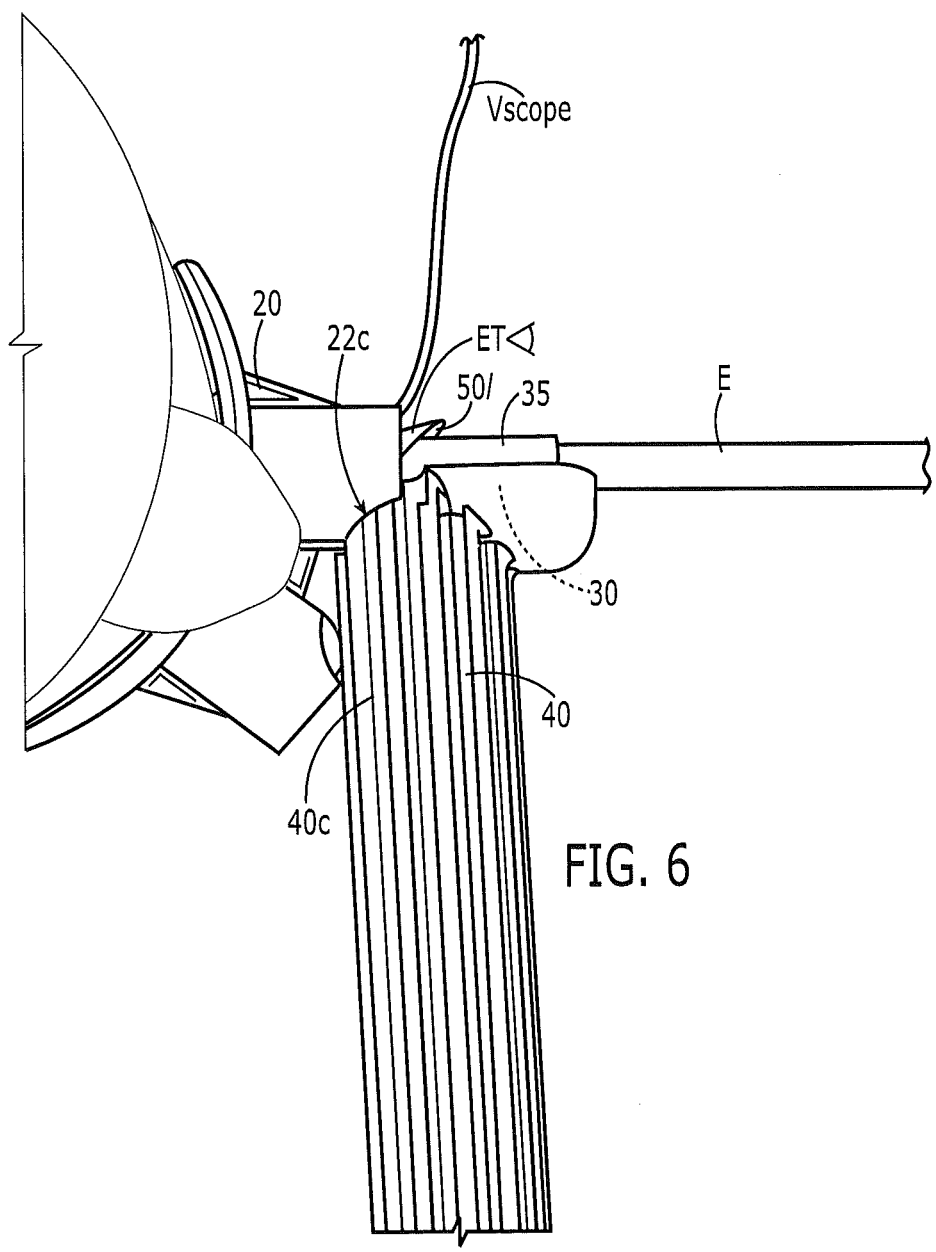
FIG. 6 is a top perspective view of the device shown in FIG. 4A according to embodiments of the present invention.

The endoscope E can remain in position in the patient during the change out of the ET tubes. As shown in FIG. 3, a new ET tube 50new can reside on the endoscope E above the "old" ET tube 50old that is being replaced so that the new tube 50new can be slid down over the endoscope E (which acts as a guidewire), typically after the handle 40 (where used) is at least partially removed so as to not occlude the travel path to position the new tube properly in the patient once the old tube 50old has been removed from the patient. FIGS. 4A, 4B and 6 illustrate that a viewing scope lead (Vscope) can also be in position during the procedure.

FIGS. 1-3, for example, show that the device 10 can include a handle 40 that can engage the mouthpiece 20. However, a user may directly apply force to the mouthpiece or to a grip member that holds the endoscope E, which may not require the use of a handle 40.

However, in particular embodiments, the handle 40 is typically configured to releasably engage the mouthpiece 20. However, in some embodiments, the handle 40 can be permanently attached to the mouthpiece. Referring to FIG. 3, the handle 40 can have any suitable length "L" but is typically between 2-10 inches such as about 3 inches, about 4 inches, about 5 inches, about 6 inches, about 7 inches, about 8 inches, about 9 inches or about 10 inches. The handle can have a width "W" that is between about 0.25 inches to about 2 inches, typically about 1 inch. As shown in FIG. 1, the handle 40 can have an elongate primary body (arm) 40a with an arcuate profile 40p when viewed from the end and may also have a distal end that is substantially orthogonal to the arm 40a which has a semi-circular curved shape 40c.

The mouthpiece 20 can have a substantially rigid or semi-rigid monolithic body. The mouthpiece 20 can alternately comprise components that snap together or apart, such as components that reside on either side of the short tube 20t (where used) or channel 20c to provide a seam about the channel 20c for easy installation or removal about a respective ET tube thereat.

In operation, a user can push down on the handle 40 to apply a force $F_H$ (FIG. 4A) while the ET tube 50 is pulled out. The ET tube is typically pulled out by a different clinician (e.g., doctor or nurse) from the clinician applying the force $F_H$. The person withdrawing the old tube 50 can use fingers and/or forceps to attach to and pull the "old" ET tube 50 upward with a force direction $F_{ET}$ to slit the outer wall 50w of the respective tube using the cutting blade 30 to remove the old tube 50 while the endoscope E remains in position. The person removing the tube 50 can use a pulling direction that is at an angle θc that is toward the cutting blade 30 (toward the handle in the configuration shown in FIGS. 1-4, for example).

Figure 5:
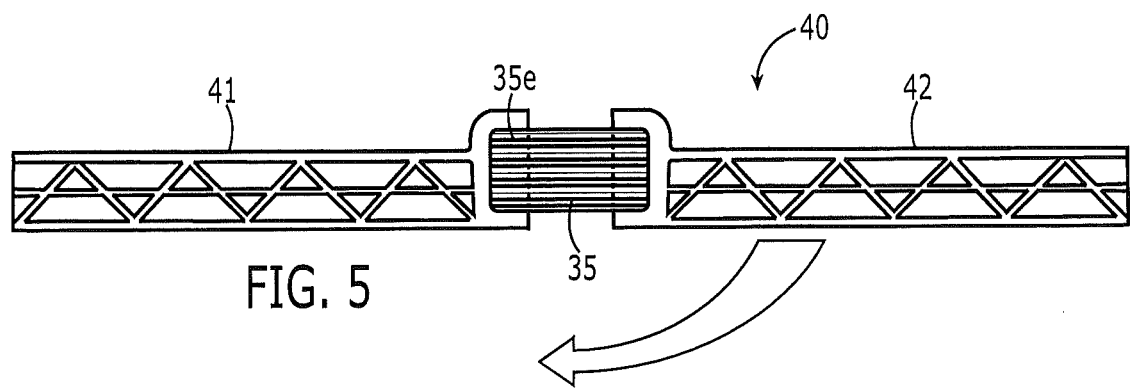
FIG. 5 is a schematic illustration of an exemplary configuration of a handle according to embodiments of the present invention.

As shown in FIGS. 1 and 5, the handle 40 can have first and second matably attachable elongate members 41, 42 that can attach together before or after one or both are attached to the mouthpiece 20. In other configurations, the handle 40 has a single piece body.

The device 10 can optionally also include a grip member 35 that snugly attaches to the endoscope E to hold the endoscope E in position (and substantially if not totally stationary) in response to the holding force $F_H$ being applied while a clinician pulls the old tube 50old up to remove it from the patient. Typically, the grip member 35 extends out from a distal end of the handle 40d. The grip member 35 can be a flexible (e.g. polymeric or rubber) strap with opposing sides held by distal end portions 40d of the different handle members 41, 42. The grip member 35 can have any suitable length but is typically between about 0.25-2 inches such as between about 0.5 to about 1 inch, including, for example, about 0.8 inches in some embodiments. A user can also or alternatively manually directly hold the endoscope E or use other devices for same.

FIG. 5 illustrates that the grip member 35 is held by the distal end portions of the handle members 41, 42. In use, a user can wrap the grip member 35 about the endoscope E, then close the members 41, 42 together (typically via snap fit or other frictional engagement) to hold the endoscope E snugly inside the grip member 35. One or both ends of the grip member 35 can be pulled to tighten the hold (and/or adjust the grip member length). However, other grip member configurations can be used. For example, the grip member 35 can be directly mounted to the mouthpiece 20 instead of the handle 40 or can comprise cooperating components that are held by both the handle 40 and mouthpiece 20. The grip member 35 can be configured as a clamp or a molded plastic or semi-rigid polymeric member that is scored with geometric shapes so as to be able to bend about the endoscope E. The grip member 35 can be provided as a separate member that releasably attaches to the handle or is used by a clinician separate from the mouthpiece or handle. The grip member 35 can reside partially about the outer wall of the endoscope or entirely as shown in FIG. 6, for example.

Figure 8:
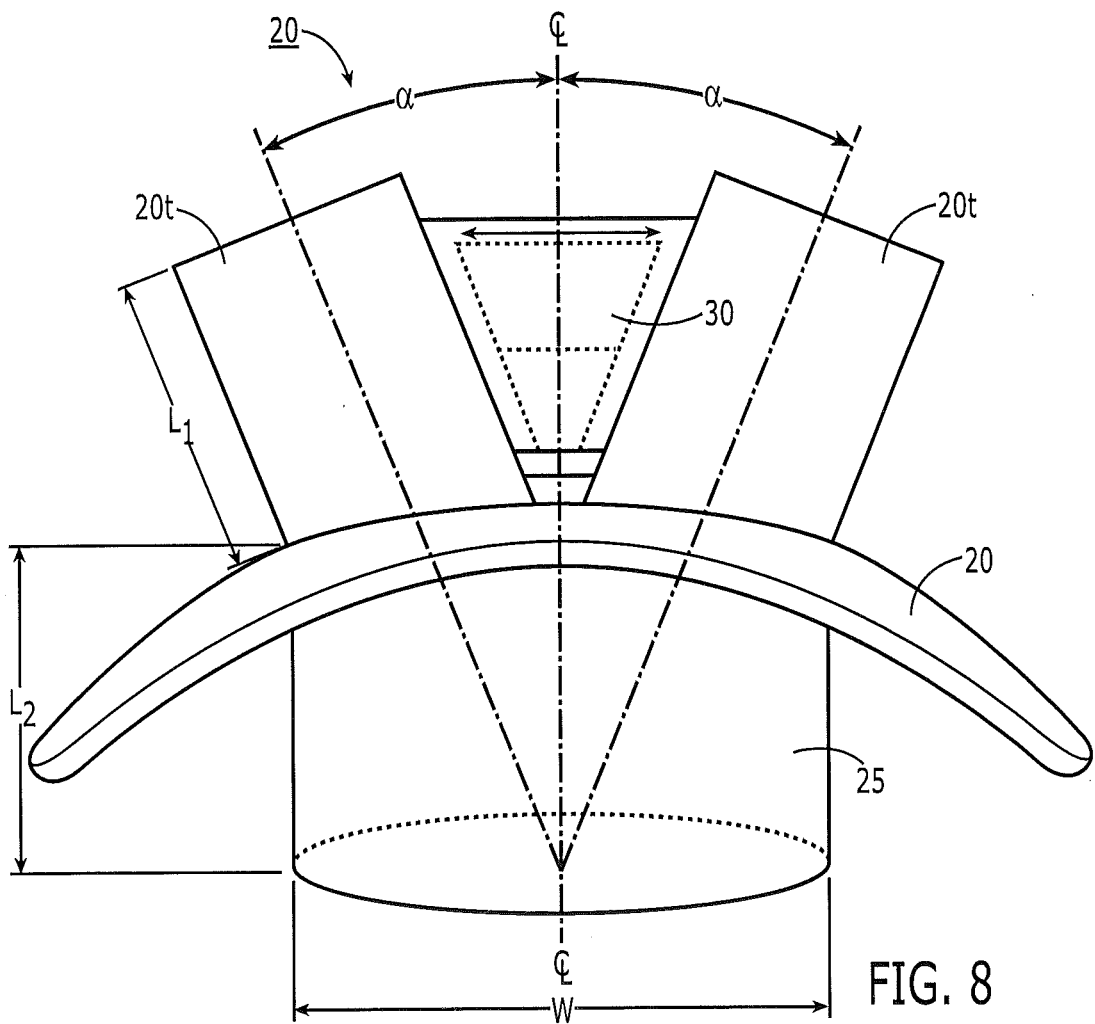
FIG. 8 is an enlarged view of an exemplary mouthpiece suitable for use with the tracheal assembly according to embodiments of the present invention.

As shown in FIGS. 3 and 4A, for example, the cutting blade 30 can reside in the handle 40 so that, when in position, a cutting edge 30e of the cutting blade 30 faces into the channel 20c to be able to cut into the outer wall 50w of the adjacent ET tube 50 as the ET tube is pulled from the patient over the endoscope E. However, it is contemplated that the cutting blade 30 can reside in other locations and/or have other configurations. For example, the cutting blade 30 can be retractable/extendable by a user rather than in a fixed location. FIG. 8 illustrates that the cutting blade 30 can reside on the mouthpiece 20 and can be configured to slide, rotate, pivot or otherwise deploy laterally into a channel 20c that holds the ET tube 50. In this embodiment, the cutting blade 30 can reside in a protective sheath or housing for safety. Where short tubes 20t are used, they can include longitudinally extending slits, slots or other access channels aligned with the cutting blade 30, so that when deployed laterally from a home position, the cutting blade 30 can extend into the tube 20t a distance sufficient to cut the outer wall 50w.

The mouthpiece 20 can be a molded monolithic body with integral short tubes 20t. Alternatively other channels and channel members can be used. In some embodiments, a short tube 20 can be matably securely attached in situ to a port or channel in the primary mouthpiece body. The short tube 20t can threadably attach, adhesively attach or snap-fit into a recess/channel in the mouthpiece body, for example.

The mouthpiece 20 can be configured for use as an ET tube holder that can include a locking clip for secure tube position and/or as a modified conventional biteblock for endoscopy. Thus, the mouthpiece 20 can be placed on the patient during the initial ET tube insertion procedure. Alternatively, the mouthpiece 20 can be a special purpose mouthpiece 20 that is used only during a replacement or change out ET tube procedure.

As shown in FIGS. 1-8, the mouthpiece 20 includes two spaced apart channels 20c provided by two short tubes 20t. During an ET replacement or change out procedure, a user can select which channel 20c (i.e., the right or left) to use, depending on user preference (which side of the patient they may reside on and/or whether the user is right or left-handed). In other embodiments, the mouthpiece 20 can have a single channel 20c (FIG. 10) and this single channel can be medially located on the mouthpiece or positioned to one side closer than the other.

As shown in FIGS. 4A and 6, for example, the handle 40 can have a distal end portion that has a curved outwardly projecting (semicircular or arcuate) shape 40c that is matably received in a substantially matably curved (semi circular) recess 22c residing in the upper (outer facing) end. The arcuate recess can have a radius of curvature that is between about 0.2 to about 0.5 inches, but other shapes and sizes of matable configurations may be used. The short tube(s) 20t can also optionally include an elongate slit 22s that resides under the curved recess 22c. The slit 22s can merge into the curved recess 22c and may allow the cutting edge 30e of the blade 30 to enter therein.

The cutting blade 30 can be configured to extend a short distance above the uppermost end of the short tube 20t, where used, typically between 0.1 to about 0.5 inches, more typically about 0.25 inches.

As shown in FIGS. 4A and 4B, the short tube 20t can also or alternatively include an outer edge with a notch 23 such as a "V" shaped notch on a side that is diametrically opposed from the curved recess 22c. FIG. 1 illustrates the mouthpiece 20 without this feature. In use, a clinician may place forceps against the ET tube 50 to pull the tube 50 upward (and typically but not required, toward the blade 30). FIG. 6 illustrates that the indwelling endotracheal tube 50 can be cut at an angle to define a leading end 50l at a position that is proximate but above the mouthpiece 20, at initiation or just prior to start the removal process.

FIG. 8 illustrates that the short tubes 20t can have a length $L_1$ and can be spaced apart and angled so that at the outer edges, the short tubes angle outward at an angle "α" that is between 15 to 45 degrees from vertical (also shown as the centerline C/L of an optional underlying biteblock 25). The short tubes 20t (where two are used) can angle outwardly at the same angle or at different angles. The short tube(s) may also be vertical. The short tubes 20t can have axially extending centerlines that are spaced apart from each other at an angle between 45 and 120 degrees at an outer end thereof.

Figures 9A, 9B:
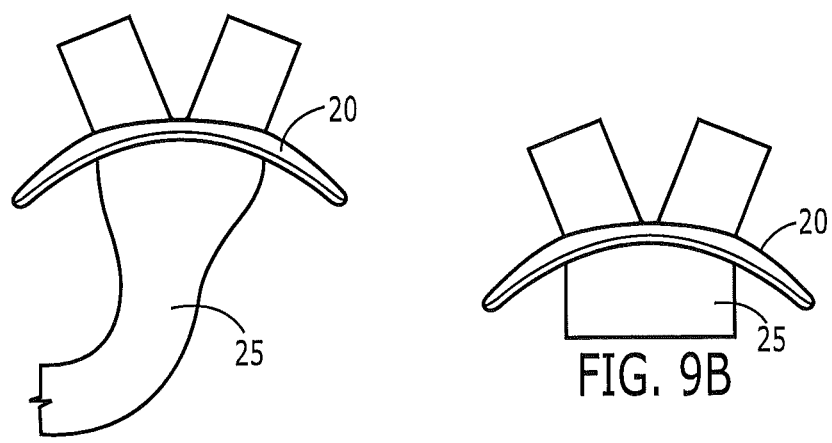
FIGS. 9A and 9B are side section schematic illustrations of different exemplary configurations of internal (bite block) configurations for the mouthpieces described herein.

The biteblock 25 can be substantially rigid or may be flexible or semi-rigid for patient comfort. The biteblock 25 can have a straight length $L_2$ that is between about 1-2 inches (for adults) and a width W that is between about 1.5 to about 2 inches (for adults). As shown in FIG. 9A, the biteblock 25 can have a radius of curvature that begins a distance inward of the external face contacting surface of the mouthpiece, after the straight segment, for a distance such as about 1-2 inches (for adults) past the straight segment. FIG. 9B illustrates that the mouthpiece 20 can include only a straight biteblock 25.

Figure 10A:
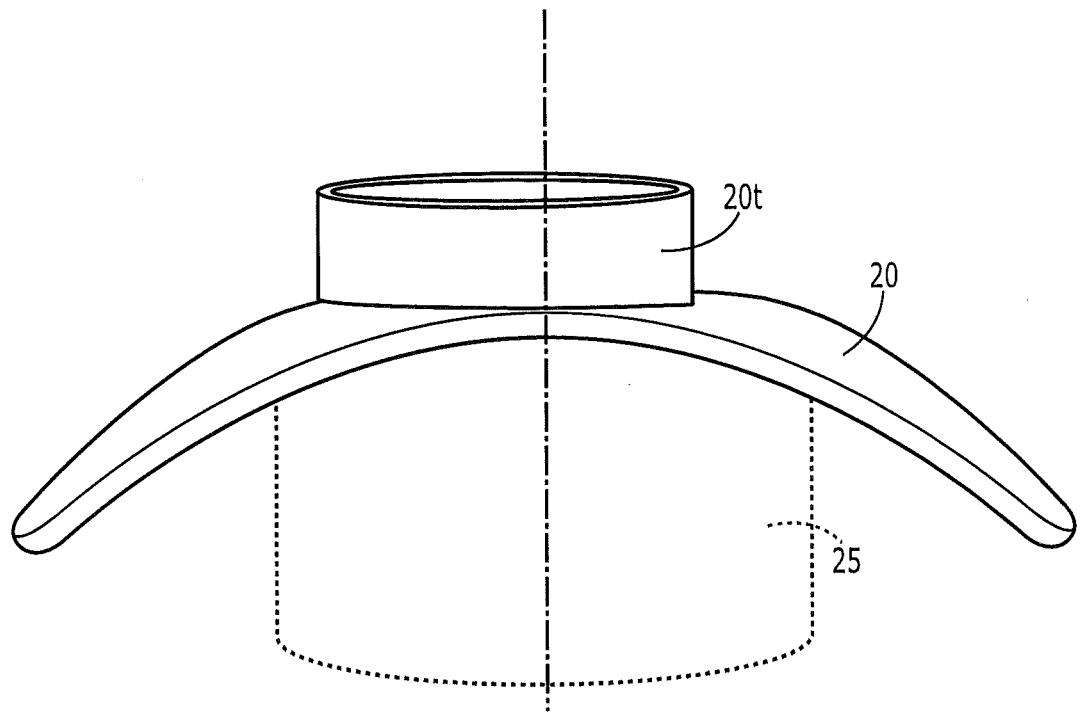
FIG. 10A is a side schematic illustration of a mouthpiece with a different configuration according to embodiments of the present invention.

FIG. 10A illustrates that the mouthpiece 20 can include a single short tube 20t and it may be substantially vertical or angled as described above with respect to the dual short tube configurations such as shown in FIG. 8.

Figure 10B:
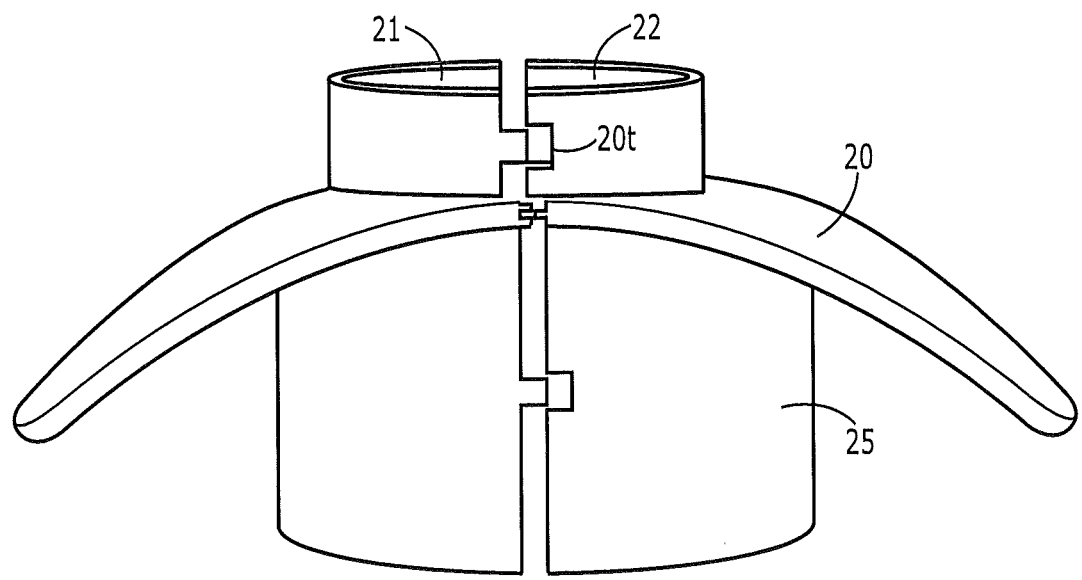
FIG. 10B is side schematic illustration of a mouthpiece with matably attachable components according to embodiments of the present invention.

FIG. 10B illustrates that the mouthpiece 20 can comprise matably attachable members 21, 22 that can be attached in situ about an indwelling ET tube 50 according to particular embodiments of the present invention.

FIG. 11 illustrates an exemplary interior surface modification of a channel 20c to facilitate tight connection with the ET tube 50 and alignment with a cutting blade 30. The surface modifications shown include resilient fingers but other friction enhancing configurations that still allow for sliding of the ET tube 50 may be used including, for example, coatings, embossed surfaces and the like or combinations of the above.

FIGS. 12A-12C illustrate another embodiment of the tracheal assembly 10. As shown in FIG. 12A, the tracheal assembly device 10 includes a mouthpiece 20 with at least one open channel 20c and tube or post 20t that cooperates with a cutting blade 30' held by a handle 40. The top of the handle 40t can be sized and configured to abut against the endoscope E. The cutting blade 30' can comprise a unitary, substantially rectangular-shaped band 30b of surgical grade metal, e.g., stainless steel, that can wrap around a particular size fiberoptic scope E. When wrapped around the scope E, the band 30b can tightly grasp the scope E and define a cylindrical channel 30ch (FIG. 12C). The band 30b can be formed in situ or prior to use (e.g., "pre-formed") to wrap about its long axis "L" to form the cylindrical channel 30ch.

In some embodiments, the band 30b comprise a thin, sufficiently strong, malleable metallic material such as a metal shape memory material. The band 30b can be provided pre-formed and sized for particular scopes. The band 30b can be formed in situ or on site corresponding to the scopes E at that facility and in use.

The band 30b can also have other shapes. Non-cutting edges may be coated with a protective (spongy, foam-like material, rubber or other) material to inhibit user exposure to sharp edges.

In position, one or both of the two trailing sides 31, typically only one of the trailing sides 31 emanating from the scope E forms the flat cutting edge 30c, extending between about 2-10 mm from the scope edge. The two long sides of the band 30b can have a length sufficient to continue upward another 10-40 mm, typically about 20 mm, each side firmly anchored to each half of the handle 40. As shown in FIG. 12B, one long side of the band 30b can have a first segment $31_1$ that extends a further distance down (relative to the orientation shown) than a second segment $31_2$. The first segment $31_1$ defines the cutting edge 30c.

The handle 40 can include two matable halves that can be configured to have a releasable engagement with the cutting band 30b and can have secure-alignment features 40f with the band alignment feature 30f (e.g., male-female features, pins/holes and the like), so that a clinician can effect substantially instant or quick release of the two halves after cutting is complete. As shown in FIG. 12C, the band 30b, when wrapped, includes a planar length 30h of fastening surface that attaches to the handle 40.

The semi-circular distal and inferior end of the cutting handle 40 can have groove 40g which snugly mates with an inner rim 22r of the mouthpiece (oral guide) short tube 20t. The upper part of the distal handle 40u that secures the cutting band 30c can be configured to closely approximate the cylindrical channel 30ch, nearly touching the scope E. The inferior part of the distal handle can be notched to expose the cutting edge 30c of the metal band 30b, and the superior portion of the notch can form a V to facilitate ETT 50 separation upon extraction as it is cut away.

In this embodiment, the inner rim of the tube 20t is not required to have a vertical slit for any cutting blade and there is no longer any inferiorly-protruding cutting blade (such as the cutting blade 30 from the embodiments shown with respect to FIGS. 3 and 4A). A lateral portion of the post or tube 20t can have an open window or side 20a that allows physical access to the ETT to facilitate grasping the ETT with the clamp C (e.g., a Kocher Clamp).

The cutting band 30b can be precision cut/sized according a corresponding (exact or within some tight tolerance) size (thickness/diameter) of the fiberoptic scopes E on hand at any institution. The cutting band 30b can accommodate a range of scopes E from thin to thick scopes (e.g., 5.7 mm, 6.0 mm diameters). Alternately, model/size specific bands 30b can be provided.

Embodiments of the invention can be carried out to maintain visualization (through the endoscope) of the carina (the distal end of the trachea that splits to right and left lung bronchi), while concurrently and also maintaining direct access within the trachea during the exchange process. This combination gives the clinician the reassurance that access, depth, stability, and pathway will not be compromised during the exchange.

Thus, the invention fills a long felt need that addresses the deficiencies and problems in conventional exchanges which could be frightening and dangerous, particularly in swollen or obese patients, or those with otherwise difficult intubations. In the past, typically, the old tube must be pulled out blindly over an exchange rod, tube or bougie, and then the new tube is slid over the bougie blindly and without stability. One may lose access to the trachea as the rod, tube or bougie, inadvertently, slides in/out, or kinks into the esophagus, or it may go in too far and puncture the bronchus.

Thus, the methods and devices contemplated by embodiments of the invention are configured so that the pathway is not lost and the sight of the pathway inside the trachea during the exchange is maintained.

It is contemplated that such tubes can be changed out as needed for malfunction or for size change, or on any schedule deemed appropriate by medical care.

In some embodiments, such as where the mouthpiece is a "special purpose" mouthpiece used for the change out, the procedure can be carried out as follows. The mouthpiece 20 is put in place (threaded or slid over) the indwelling ET tube 50, after removing the ET adaptor, allowing it to protrude from one of the holes 20c (allowing a user to select, as there are typically two apertures/channels to accommodate left/right handed users and/or to allow the procedure to be done from the other side of the patient). A new ET tube is (previously) preloaded onto a long endoscope. The endoscope is then pushed through the old indwelling ET tube (so the endoscope has both the new and old ET tubes on it).

Then the handle 40 with cutting blade 30c from long edge 31 of formed band 30b (FIGS. 12A-12C) is wrapped around the shaft of the scope between the two ET tubes. The handle is anchored to the mouthpiece tube 20t via groove 40g at the upper rim 20t. Then the old ET tube 50old is grabbed with forceps and pulled up. As it is pulled up, it is slit open longitudinally by the cutting blade 30, so that the old ET tube peels off to the side. During this time, the endoscope is still in the patient's airway providing direct continuous visualization of the carina by the clinician. Then, the handle 40 is removed and the new ET tube 50new (which has been at the top of the endoscope this whole time) is slid down the endoscope E and into the airway, as it would be during any typical and common fiberoptic intubation.

It is noted that where the embodiment of FIG. 3 or 4A, for example, are used, the handle 40 and grip are positioned in lieu of the wrapped band to form the cutting as described above so that the cutting blade 30 contacts the old ET tube 50old.

Figure 13:
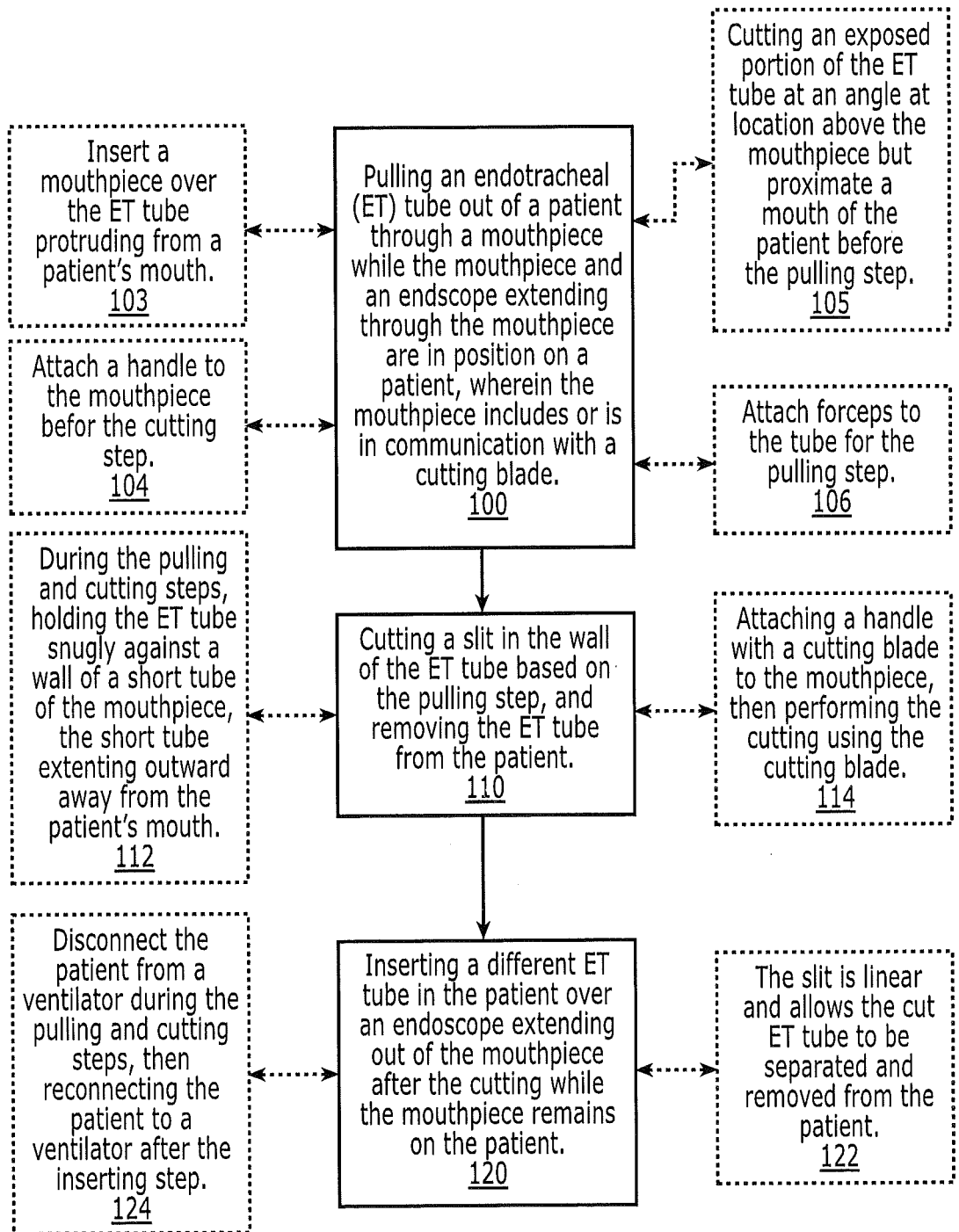
FIG. 13 is a flow chart of exemplary operations that can be used according to embodiments of the present invention.

FIG. 13 illustrates exemplary steps that can be used to rapidly remove and replace an endotracheal tube (typically in under about 1 minute). An endotracheal (ET) tube can be pulled out of patient through a mouthpiece while the mouthpiece and an endoscope extending through the mouthpiece are in position on a patient, wherein the mouthpiece includes or is in communication with a cutting blade (block 100). A slit can be cut in the wall of the ET tube based on the pulling step and removing the ET from the patient (block 110). A different ET tube is inserted over the endoscope into the patient after the cutting while the mouthpiece remains on the patient (block 120).

The mouthpiece can be inserted into the patient's mouth over an indwelling ET tube protruding from a patient's mouth (block 103). A handle can be attached to the mouthpiece before the cutting step (block 104).

An exposed portion of the ET tube can be cut at an angle at a location above the mouthpiece but proximate the mouth before the pulling step (block 105).

Forceps can be attached to the ET tube for the pulling step (block 106).

During the pulling and cutting steps, the ET tube can be snugly held against a wall of a short tube of the mouthpiece, the short tube extending outward away from the patient's mouth (block 112).

The patient can be disconnected from a ventilator during the pulling and cutting steps, then reconnected after the inserting step (block 124). A handle with a cutting blade can be attached to the mouthpiece, then the cutting can be performed using the cutting blade in the handle (block 114). The slit can be linear and allows the cut ET tube to be separated and removed from the patient (block 122) while the endoscope remains in position.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

That which is claimed:

1. A tracheal assembly medical device, comprising:
   a mouthpiece sized and configured to allow an endotracheal tube to extend outwardly therefrom;
   a cutting blade in communication with an outwardly facing portion of the mouthpiece; and
   a handle with first and second matably connecting members that attach together and hold the cutting blade, wherein the handle releasably engages the mouthpiece.

2. The device of claim 1, wherein the mouthpiece comprises at least one outwardly projecting substantially rigid short tube defining an open channel, wherein the short tube is configured to allow the endotracheal tube to slidably move therethrough.

3. The device of claim 1, wherein the mouthpiece comprises spaced apart first and second short tubes, each defining an open channel, wherein the handle has one end that is sized to releasably engage a selected one of the at least one short tubes, and wherein, when engaged with a respective selected one of the short tubes, the handle extends substantially orthogonal to a centerline of the engaged short tube.

4. The device of claim 1, wherein the mouthpiece has a monolithic unitary body with an inwardly extending bite block and a pair of outwardly extending short tubes.

5. The device of claim 4, wherein the short tubes have axially extending centerlines that are spaced apart at an angle between 45 and 120 degrees at an outer end thereof.

6. The device of claim 1, wherein the mouthpiece further comprises at least one outwardly extending substantially rigid short tube, wherein the handle further comprises a grip member that snugly holds an outerwall of an endoscope extending through the short tube inside the endotracheal tube, wherein the short tube a curved upper edge portion, and wherein the handle is configured to reside against the short tube with an end portion of the handle residing in the curved upper edge portion of the short tube.

7. The device of claim 1, wherein a cutting edge of the cutting blade faces an outwardly projecting short tube of the mouthpiece with the endotracheal tube and an endoscope residing therein, and wherein the cutting blade extends a distance of between about 0.1 inches to about 2 inches above an upper end of the short tube.

8. The device of claim 1, wherein the mouthpiece comprises at least one outwardly projecting substantially rigid short tube defining an open channel, wherein the short tube is configured to allow the endotracheal tube to extend outwardly therefrom, and wherein an outer end portion of the short tube has (i) a first side with a curved end that merges into a downwardly extending slit and (ii) a second side with a substantially "V" shaped notch, with the open end of the V facing up.

9. The device of claim 1, wherein the cutting blade is configured as a malleable unitary surgical metallic band that wraps together to define a cylindrical channel that snugly encases an outerwall of an endoscope.

10. A medical device, comprising:
    a mouthpiece with at least one outwardly projecting substantially rigid short tube defining an open channel, wherein one of the at least one short tube is configured to allow an endotracheal tube to extend outwardly therefrom; and
    a handle comprising a cutting blade configured to reside against the mouthpiece short tube so that the cutting blade resides adjacent the endotracheal tube extending therefrom with the cutting blade extending a distance above the mouthpiece short tube, wherein the cutting blade is defined by a malleable unitary surgical metal band that wraps together to define a cylindrical channel that snugly encases an outerwall of an endoscope.

11. The device of claim 10, wherein (a) the handle further comprises a grip member configured to engage an endoscope residing inside the endotracheal tube at a location above the respective short tube and/or (b) the cutting blade is a surgical metal band that has a cylindrical channel that snugly abuts an endoscope residing inside the endotracheal tube at a location above the respective short tube.

12. The device of claim 10, wherein the mouthpiece comprises spaced apart first and second short tubes, each defining an open channel, and wherein, when in operative position, the handle extends substantially orthogonal to a centerline of the attached short tube.

13. The device of claim 10, wherein the mouthpiece has a monolithic unitary body with an inwardly extending bite block and the at least one substantially rigid short tube is a pair of spaced apart outwardly extending short tubes, and wherein the short tubes have axially extending centerlines that are spaced apart at an angle between 45 and 120 degrees at an outer end thereof.

14. The device of claim 10, wherein the handle comprises first and second matably attachable components that position a grip member proximate to but above one of the at least one short tube.

15. The device of claim 10, wherein the at least one short tube has a slit that merges into a curved outer edge portion, and wherein the handle is configured to reside against the short tube with a portion residing in the curved outer edge portion of the short tube.

16. The device of claim 10, wherein a cutting edge of the cutting blade faces the short tube with the endotracheal tube and an endoscope residing therein, and wherein the cutting blade extends a distance of between about 0.1 inches to about 2 inches above an end of the at least one short tube.

17. The device of claim 10, wherein an outer end portion of the at least one short tube has an inner facing side with a curved end that merges into a downwardly extending slit.

18. The device of claim 10, wherein an outer end portion of the at least one short tube has an outer facing side with a substantially "V" shaped notch, with the open end of the V facing up.

19. A method of changing an endotracheal tube, comprising:
attaching a handle to a mouthpiece while the mouthpiece is in position on a patient, wherein the handle holds a cutting blade;
cutting an exposed portion of an endotracheal (ET) tube extending out of the patient at an angle; then
pulling the endotracheal (ET) tube out of trachea of the patient through the mouthpiece while the mouthpiece is in position on the patient with an endoscope extending therethrough and with the handle attached to the mouthpiece;
cutting a slit in the wall of the ET tube based on the pulling step using the cutting blade;
removing the ET tube from the patient; then
inserting a different ET tube in the patient over the endoscope while the mouthpiece remains on the patient, allowing change out of the ET tube while (i) maintaining visualization through the endoscope of a carina at a distal end of the trachea that splits to right and left lung bronchi and concurrently (ii) maintaining direct access within the trachea during the exchange process to thereby provide a clinician reassurance that access and pathway and stability will not be compromised during the exchange.

20. The method of claim 19, wherein the attaching is carried out to position a cutting edge of the cutting blade adjacent an outerwall of the ET tube.

21. The method of claim 19, wherein the cutting the slit is carried out at a location that is proximate to but above an outwardly projecting short tube of the mouthpiece.

22. The method of claim 19, wherein the pulling is carried out by attaching forceps to the ET tube above a short tube of the mouthpiece or at a top portion of the short tube and pulling at an angle with respect to the short tube to split the ET tube as it contacts the cutting blade, and wherein the removing and inserting steps are carried out in under 1 minute.

23. The method of claim 19, wherein the cutting blade is defined by a malleable surgical metal band that wraps together to define a cylindrical channel, and wherein the method further comprises placing the metal band about an outerwall of an endoscope so that the endoscope resides snugly in the cylindrical channel before cutting the slit.

\* \* \* \* \*